US009101740B2

(12) United States Patent
Serna et al.

(10) Patent No.: US 9,101,740 B2
(45) Date of Patent: Aug. 11, 2015

(54) PROCESS FOR FOLDING DRUG COATED BALLOON

(71) Applicant: Abbott Laboratories, Santa Clara, CA (US)

(72) Inventors: Benjamyn Serna, Gilroy, CA (US); Binh Nguyen, Newark, CA (US)

(73) Assignee: ABBOTT LABORATORIES, Santa Clara, CA (US)

( * ) Notice: Subject to any disclaimer, the term of this patent is extended or adjusted under 35 U.S.C. 154(b) by 0 days.

(21) Appl. No.: 14/200,498

(22) Filed: Mar. 7, 2014

(65) Prior Publication Data

US 2014/0188045 A1    Jul. 3, 2014

Related U.S. Application Data

(62) Division of application No. 12/882,953, filed on Sep. 15, 2010, now Pat. No. 8,702,650.

(51) Int. Cl.
| *A61M 31/00* | (2006.01) |
| *A61M 25/10* | (2013.01) |
| *A61L 29/08* | (2006.01) |
| *A61L 29/16* | (2006.01) |

(52) U.S. Cl.
CPC ............ *A61M 25/1027* (2013.01); *A61L 29/08* (2013.01); *A61L 29/16* (2013.01); *A61M 25/1029* (2013.01); *A61M 2025/1031* (2013.01)

(58) Field of Classification Search
CPC ... A61L 31/16; A61L 29/08; A61L 2300/606; A61L 29/16; A61L 2300/00; A61L 2420/00; A61L 2420/02; A61M 25/1029; A61M 2025/1031; A61M 2025/105; A61M 25/1027; A61M 25/0045; A61M 25/10; A61B 17/12136

USPC ..................................................... 604/103.02
See application file for complete search history.

(56) References Cited

U.S. PATENT DOCUMENTS

| 4,743,465 A | 5/1988 | Saeki et al. |
| 4,748,982 A | 6/1988 | Horzewski et al. |
| 5,300,085 A | 4/1994 | Yock |
| 5,370,614 A | 12/1994 | Amundson et al. |
| 5,464,650 A | 11/1995 | Berg et al. |
| 5,496,346 A | 3/1996 | Horzewski et al. |
| 5,591,227 A | 1/1997 | Dinh et al. |
| 5,626,600 A | 5/1997 | Horzewski et al. |
| 5,649,977 A | 7/1997 | Campbell |
| 5,911,452 A | 6/1999 | Yan |

(Continued)

OTHER PUBLICATIONS

U.S. Appl. No. 12/882,953, Dec. 9, 2013 Notice of Allowance.

(Continued)

*Primary Examiner* — Jason Flick
(74) *Attorney, Agent, or Firm* — Baker Botts L.L.P.

(57) ABSTRACT

Device, system, method of coating an expandable member is provided. The method comprises providing an expandable member with a plurality of folds defined therein, the expandable member having a folded configuration and a fully expanded configuration at a rated nominal pressure. The expandable member is inflated to an initial pressure of from 10% to about 300% of nominal pressure. A therapeutic agent is disposed on at least a portion of the expandable member. The expandable member is partially deflated to an intermediate pressure by withdrawing an amount of inflation medium from the expandable member, and by applying an external force to the expandable member.

22 Claims, 4 Drawing Sheets

(56) References Cited

U.S. PATENT DOCUMENTS

| | | | |
|---|---|---|---|
| 5,980,972 | A | 11/1999 | Ding |
| 6,120,847 | A | 9/2000 | Yang et al. |
| 6,141,855 | A | 11/2000 | Morales |
| 6,406,457 | B1 | 6/2002 | Wang et al. |
| 6,478,807 | B1 | 11/2002 | Foreman et al. |
| 6,494,906 | B1 | 12/2002 | Owens |
| 6,669,980 | B2 | 12/2003 | Hansen |
| 6,676,987 | B2 | 1/2004 | Zhong et al. |
| 6,743,462 | B1 | 6/2004 | Pacetti |
| 7,241,344 | B2 | 7/2007 | Worsham et al. |
| 7,335,227 | B2 | 2/2008 | Jalisi |
| 7,378,105 | B2 | 5/2008 | Burke et al. |
| 7,445,792 | B2 | 11/2008 | Toner et al. |
| 7,455,876 | B2 | 11/2008 | Castro et al. |
| 7,488,337 | B2 | 2/2009 | Saab et al. |
| 7,504,125 | B1 | 3/2009 | Pacetti et al. |
| 7,524,527 | B2 | 4/2009 | Stenzel |
| 8,632,837 | B2 | 1/2014 | Gong et al. |
| 8,647,702 | B2 | 2/2014 | Shen et al. |
| 8,702,650 | B2 | 4/2014 | Serna et al. |
| 2001/0021419 | A1 | 9/2001 | Luthje et al. |
| 2004/0062875 | A1 | 4/2004 | Chappa et al. |
| 2004/0073284 | A1 | 4/2004 | Bates et al. |
| 2004/0122465 | A1 | 6/2004 | McMurtry et al. |
| 2004/0234748 | A1 | 11/2004 | Stenzel |
| 2005/0158449 | A1 | 7/2005 | Chappa |
| 2005/0196518 | A1 | 9/2005 | Stenzel |
| 2005/0233061 | A1 | 10/2005 | Schwarz |
| 2006/0069427 | A1 | 3/2006 | Savage et al. |
| 2007/0031611 | A1 | 2/2007 | Babaev |
| 2007/0088255 | A1 | 4/2007 | Toner et al. |
| 2007/0179591 | A1 | 8/2007 | Baker et al. |
| 2008/0113081 | A1* | 5/2008 | Hossainy et al. ............... 427/2.1 |
| 2009/0226598 | A1 | 9/2009 | Feng et al. |
| 2010/0023108 | A1 | 1/2010 | Toner et al. |
| 2010/0030183 | A1 | 2/2010 | Toner et al. |
| 2010/0040766 | A1 | 2/2010 | Chappa et al. |
| 2010/0055294 | A1 | 3/2010 | Wang et al. |
| 2011/0151199 | A1 | 6/2011 | Nelson et al. |
| 2011/0281019 | A1 | 11/2011 | Gong et al. |
| 2011/0281020 | A1 | 11/2011 | Gong et al. |
| 2012/0022540 | A1* | 1/2012 | Chasmawala et al. .......... 606/90 |
| 2012/0064223 | A1 | 3/2012 | Gamez et al. |
| 2012/0065583 | A1 | 3/2012 | Serna et al. |
| 2012/0128863 | A1 | 5/2012 | Nguyen et al. |
| 2012/0143054 | A1* | 6/2012 | Eaton et al. .................... 600/435 |
| 2012/0315374 | A1 | 12/2012 | Nguyen et al. |
| 2012/0315375 | A1 | 12/2012 | Shen et al. |
| 2012/0315376 | A1 | 12/2012 | Nguyen et al. |
| 2014/0113059 | A1 | 4/2014 | Shen et al. |

OTHER PUBLICATIONS

U.S. Appl. No. 12/882,953, Nov. 15, 2013 Request for Continued Examination (RCE).
U.S. Appl. No. 12/882,953, Oct. 28, 2013 Advisory Action.
U.S. Appl. No. 12/882,953, Oct. 16, 2013 Response to Final Office Action.
U.S. Appl. No. 12/882,953, Aug. 16, 2013 Final Office Action.
U.S. Appl. No. 12/882,953, Apr. 12, 2013 Response to Non-Final Office Action.
U.S. Appl. No. 12/882,953, Mar. 28, 2013 Applicant Initiated Interview Summary.
U.S. Appl. No. 12/882,953, Jan. 15, 2013 Non-Final Office Action.
U.S. Appl. No. 12/882,953, Dec. 21, 2012 Response to Restriction Requirement.
U.S. Appl. No. 12/882,953, Nov. 28, 2012 Restriction Requirement.
U.S. Appl. No. 12/882,990, Dec. 2, 2013 Amendment and Request for Continued Examination (RCE).
U.S. Appl. No. 12/882,990, Oct. 11, 2013 Advisory Action.
U.S. Appl. No. 12/882,990, Oct. 1, 2013 Response to Final Office Action.
U.S. Appl. No. 12/882,990, Aug. 1, 2013 Final Office Action.
U.S. Appl. No. 12/882,990, Apr. 8, 2013 Response to Non-Final Office Action.
U.S. Appl. No. 12/882,990, Dec. 6, 2012 Non-Final Office Action.
U.S. Appl. No. 13/158,101, Oct. 7, 2013 Notice of Allowance.
U.S. Appl. No. 13/158,101, Sep. 17, 2013 Supplemental Amendment and Statement of the Substance of the Interview.
U.S. Appl. No. 13/158,101, May 24, 2013 Response to Restriction Requirement.
U.S. Appl. No. 13/158,101, Apr. 26, 2013 Restriction Requirement.
U.S. Appl. No. 13/158,057, Oct. 10, 2014 Notice of Allowance.
U.S. Appl. No. 13/158,057, Apr. 1, 2014 Request for Continued Examination (RCE).
U.S. Appl. No. 13/158,057, Oct. 24, 2013 Applicant Initiated Interview Summary.
U.S. Appl. No. 13/158,057, Sep. 12, 2013 Non-Final Office Action.
U.S. Appl. No. 13/158,057, May 24, 2013 Response to Restriction Requirement.
U.S. Appl. No. 13/158,057, Apr. 26, 2013 Restriction Requirement.
U.S. Appl. No. 13/280,607, Apr. 26, 2013 Statement Substance of Interview.
U.S. Appl. No. 13/108,283, Nov. 12, 2013 Issue Fee payment.
U.S. Appl No. 13/108,283, Aug. 12, 2013 Notice of Allowance.
U.S. Appl. No. 13/108,283, Jun. 28, 2013 Response to Non-Final Office Action.
U.S. Appl. No. 13/108,283, Mar. 28, 2013 Non-Final Office Action.
U.S. Appl. No. 13/109,156, Oct. 7, 2014 Notice of Allowance.
U.S. Appl. No. 13/109,156, Apr. 2, 2014 Request for Continued Examination (RCE).
U.S. Appl. No. 13/109,156, Oct. 25, 2013 Applicant Initiated Interview Summary.
U.S. Appl. No. 13/109,156, Sep. 10, 2013 Non-Final Office Action.
U.S. Appl. No. 13/109,156, May 24, 2013 Response to Restriction Requirement.
U.S. Appl. No. 13/109,156, Apr. 26, 2013 Restriction Requirement.
U.S. Appl. No. 14/078,212, Jun. 4, 2014 Non-Final Office Action.
U.S. Appl. No. 13/158,131, Sep. 29, 2014 Final Office Action.
U.S. Appl. No. 13/158,131, Mar. 13, 2014 Non-Final Office Action.
U.S. Appl. No. 13/280,067, Sep. 25, 2014 Non-Final Office Action.
Vivekanandhan, et al., "Computer-Aided Torch Trajectory Generation for Automated Coating of Parts with Complex Surfaces", *Journal of Thermal Spray Technology*, 3(2):208-215 (1994).
Cornell, Maintaining Distance Using Sonar video, Youtube (2010) http://www.youtube.com/watch?v=Pj6Jxo2SQgw, [Downloaded on Sep. 16, 2013].
PlumbingSupply.com, "Pipe Hangers and Brackets", (Feb. 2001), www.plumbingsupply.com/pipehangers.htlm.
Unverdoben, Martin, "The Paclitaxel-Eluting PTCA-Balloon Catheter in Coronary Artery Disease PEPCAD I-SVD PEPCAD II-ISR", Clinical Research Institute, Center for Cardiovascular Diseases, 2005-2006, Rotenburg/Fulda, Germany.

* cited by examiner

PROCESS FOR FOLDING DRUG COATED BALLOON

CROSS REFERENCE TO RELATED APPLICATIONS

This application is a divisional of U.S. application Ser. No. 12/882,953, entitled "Process For Folding Of Drug Coated Balloon" filed on Sep. 15, 2010, the contents of which is hereby incorporated by reference in its entirety.

BACKGROUND OF THE DISCLOSED SUBJECT MATTER

1. Field of the Disclosed Subject Matter

The presently disclosed subject matter is related to coating interventional medical devices, and particularly coating of therapeutic agents on an expandable member of a medical device. More particularly, the presently disclosed subject matter relates to a system and method for retaining a therapeutic agent on a balloon during folding and assembly of the medical device.

2. Description of Related Subject Matter

Atherosclerosis is a disease affecting arterial blood vessels. It is a chronic inflammatory response in the walls of arteries, which is in large part due to the accumulation of lipid, macrophages, foam cells and the formation of plaque in the arterial wall. Atherosclerosis is commonly referred to as hardening of the arteries, although the pathophysiology of the disease manifests itself with several different types of lesions ranging from fibrotic to lipid laden to calcific. Angioplasty is a vascular interventional technique involving mechanically widening an obstructed blood vessel, typically caused by atherosclerosis.

During angioplasty, a catheter having a folded balloon is inserted into the vasculature of the patient and is passed to the narrowed location of the blood vessel, at which point the balloon is inflated to a fixed size as a result of fluid pressure inside the balloon. Percutaneous coronary intervention (PCI), commonly known as coronary angioplasty, is a therapeutic procedure to treat the stenotic coronary arteries of the heart, often found in coronary heart disease. In contrast, peripheral angioplasty, commonly known as percutaneous transluminal angioplasty (PTA), generally refers to mechanical widening of blood vessels other than the coronary arteries. PTA is most commonly used to treat narrowing of the leg arteries, especially, the iliac, external iliac, superficial femoral and popliteal arteries. PTA can also treat narrowing of veins, and other blood vessels.

Although the blood vessel is often successfully widened by angioplasty, sometimes the treated wall of the blood vessel undergoes vasospasm, or abrupt closure after balloon inflation or dilatation, causing the blood vessel to collapse after the balloon is deflated or shortly thereafter. One solution to this abrupt closure is stenting the blood vessel to prevent collapse. A stent is a device, typically a metal tube or scaffold that is inserted into the blood vessel after, or concurrently with angioplasty, to hold the blood vessel open.

While the advent of stents eliminated many of the complications of abrupt vessel closure after angioplasty procedures, within about six months of stenting, a re-narrowing of the blood vessel can form. This is a condition known as restenosis. Restenosis was discovered to be a response to the injury of the angioplasty procedure and is characterized by a growth of smooth muscle cells—analogous to a scar forming over an injury. To address this condition, drug eluting stents were developed to reduce the reoccurrence of the narrowing of blood vessels after stent implantation. A drug eluting stent is a metal stent that has been coated with a drug that is known to interfere with the process of re-narrowing of the blood vessel (restenosis). Examples of various known drug eluting stents are disclosed in U.S. Pat. Nos. 5,649,977; 5,464,650; 5,591,227; 7,378,105; 7,445,792; 7,335,227, each of which are hereby incorporated by reference in their entirety. However, a drawback of drug eluting stents is a condition known as late stent thrombosis, which is an event in which blood clots on the stent.

Drug eluting balloons are believed to be a viable alternative to drug eluting stents in the treatment of atherosclerosis. In a study which evaluated restenosis, and the rate of major adverse cardiac events such as heart attack, bypass, repeat stenosis, or death in patients treated with drug eluting balloons and drug eluting stents, the patients treated with drug eluting balloons experienced only 3.7% restenosis and 4.8% MACE (major adverse cardiac events) as compared to patients treated with drug eluting stents, in which restenosis was 20.8% and 22.0% MACE rate. See PEPCAD II study, Rotenburg, Germany.

However, drug eluting balloons present certain unique challenges. For example, the drug carried by the balloon needs to remain on the balloon during delivery to the lesion site, and released from the balloon surface to the blood vessel wall when the balloon is expanded at the lesion site. For coronary procedures, the balloon is typically inflated for less than one minute, typically about thirty seconds. The balloon can be expanded for a longer period of time for peripheral procedures although this time rarely exceeds 5 minutes. Due to the short duration of contact of the drug coated balloon surface with the blood vessel wall, the balloon coating must exhibit efficient therapeutic agent transfer and/or efficient drug release during inflation. Thus, there are challenges specific to drug delivery via a drug coated or drug eluting balloon that are not presented by a drug eluting stent.

Conventional methods of loading interventional devices with therapeutic agents often require coating the entire surface of the balloon with the therapeutic agent. Coating of the entire surface can be performed in the inflated condition. For purpose of storage and shipping, as well as delivery through vasculature, the balloon is folded when deflated. However, once coated with a therapeutic agent, the balloon can become difficult to fold and sheath for assembly of the catheter. Further, conventional equipment and processes used to achieve such folding and assembly often cause damage, loss, or contamination of the therapeutic agent, and/or can result in contamination of the equipment.

Alternatively, balloons can be coated with a therapeutic agent while in a folded condition, thereby avoiding the drawbacks listed above. However, applying a coating of a solution to a folded balloon results in only a partially coated balloon surface area which may not be desirable depending upon the needs and application. Furthermore, the entire surface area of a coating applied to the folded balloon is exposed to the blood stream during the tracking and delivery procedure, thus increasing the likelihood of losing a significant amount, if not all, of the drug coating before positioning the balloon and therapeutic agent at the desired location to commence treatment.

Thus there remains a need, and an aim of the disclosed subject matter is directed towards, a method with corresponding apparatus for assembly of an expandable member having one or more therapeutic agents coated thereon in such a manner that does not result in damage or loss of therapeutic agent, nor significant contamination of the equipment employed. Additionally, the disclosed subject matter provides a processing method for expandable member memory retention.

SUMMARY OF THE DISCLOSED SUBJECT MATTER

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims herein, as well as from the appended drawings.

To achieve these and other advantages and in accordance with the purpose of the disclosed subject matter, as embodied and broadly described, the disclosed subject matter includes a system and method for assembly of an expandable member having one or more therapeutic agents coated thereon in such a manner that does not result in damage or loss of therapeutic agent, nor significant contamination of the equipment employed.

In accordance with an aspect of the disclosed subject matter, a method of coating an expandable member is provided. In one embodiment, the expandable member is a balloon member of a catheter. The method includes providing an expandable member with a plurality of folds defined therein, with the expandable member having a folded configuration and a fully expanded configuration at a rated nominal pressure. The expandable member is inflated to an initial pressure of from about 10% to about 300% of the nominal pressure. The initial pressure is preferably from about 20% to about 100% of nominal pressure. In one embodiment, during the inflation, initial pressure of the expandable member is less than nominal pressure. In one embodiment, the initial pressure is from about 20% to about 40% of nominal pressure. In one embodiment, the nominal pressure is about 6 atmospheres to about 8 atmospheres. A therapeutic agent is disposed on at least a portion of the inflated expandable member. The expandable member is partially deflated to an intermediate pressure of from about 10% to about 50% of nominal pressure by withdrawing an initial amount of inflation medium from the expandable member, and applying an external force to the expandable member. The preferred intermediate deflation pressure is from about 10% to about 20% of nominal pressure. Preferably, the initial amount of inflation medium is withdrawn simultaneously with the application of an external force. In one embodiment, the inflation medium is a gas.

The therapeutic agent can be applied by spraying, dipping, syringe coating, electrospinning, electrostatic coating, direct coating, or a combination thereof. The therapeutic agent can be selected from the group consisting of everolimus, zotarolimus, rapamycin, biolimus, myolimus, novolimus, deforolimus, tacrolimus, temsirolimus, pimecrolimus, paclitaxel, protaxel, taxanes or a combination thereof although other fluids and therapeutic agents are contemplated.

In accordance with another aspect of the invention, withdrawing the inflation medium includes using a syringe pump. Withdrawing inflation medium includes allowing the inflation medium to release from the expandable member. In some embodiments, withdrawing inflation medium occurs at a rate of approximately 2 nil/min or less. Additionally, the intermediate pressure is from about 10% to about 50% of nominal pressure. In one embodiment, the intermediate pressure is from about 10% to about 20% of nominal pressure.

An external force can be applied to the expandable member mechanically, hydraulically or pneumatically, e.g. by a stent crimper. The external force can be applied as a substantially uniform force, applied at select locations of the expandable member, and/or include a torsional component. In one embodiment, the external force is applied to the expandable member by a stent crimper in the range of from about 0.2 to about 0.25 PSI per mm of the expandable member length.

After partially deflating the expandable member, a remaining amount of inflation medium can be withdrawn from the expandable member. For example, withdrawing the remaining amount of inflation medium can occur by drawing a vacuum on the expandable member using a vacuum box or indeflator. In some embodiments, after partially deflating the expandable member, at least a portion of the expandable member can be covered with or inserted into a sheath. A mandrel can be inserted within a lumen of the expandable member during coating and/or refolding of the expandable member.

Additionally, the disclosed subject matter includes a system for coating an expandable member having a plurality of folds defined therein, the system comprising an inflator to inflate an expandable member to an initial pressure, the initial pressure being from about 10% to about 300% of a rate nominal pressure; and a dispenser to dispose a therapeutic agent on at least a portion of an expandable member inflated to the initial pressure. A deflation station is provided to partially deflate an expandable member by reducing the pressure within the expandable member to an intermediate pressure. The deflation assembly is configured to withdraw an amount of inflation medium from the inflated expandable member and to apply an external force to an expandable member. The system can further include a mandrel within a lumen of the expandable member.

The disclosed subject matter also includes a medical device comprising an expandable member with a plurality of folds defined therein, the expandable member having a folded configuration and an expanded configuration at a rated nominal pressure, the expandable member having a surface with a coating of therapeutic agent on at least a portion thereof. The coating can be applied on the surface by inflating the expandable member to an initial pressure of from about 10% to about 300%, disposing a therapeutic agent on at least a portion of the expandable member, and partially deflating the expandable member. Partially deflating the expandable member includes withdrawing an amount of inflation medium from the expandable member and applying an external force to the expandable member.

It is to be understood that both the foregoing general description and the following detailed description are exemplary and are intended to provide further explanation of the disclosed subject matter claimed.

The accompanying drawings, which are incorporated in and constitute part of this specification, are included to illustrate and provide a further understanding of the method and system of the disclosed subject matter. Together with the description, the drawings serve to explain the principles of the disclosed subject matter.

DETAILED DESCRIPTION

Reference will now be made in detail to the various embodiments of the disclosed subject matter, examples of which are illustrated in the accompanying drawings. The method and corresponding steps of the disclosed subject matter will be described in conjunction with the detailed description of the system.

The methods and systems presented herein can be used for manufacture and assembly of medical devices, such as a drug coated balloon catheter having an expandable member with a folded configuration and a fully expanded configuration at a rated nominal pressure. The disclosed subject matter is particularly suited for coating and retaining a therapeutic agent on a folded expandable member of a medical device, without damage to the coating, during folding of the expandable member and assembly of the medical device. While the disclosed subject matter references application of a fluid, e.g. therapeutic agent, it is to be understood that a variety of coatings including polymeric, therapeutic, or matrix coatings, can be applied to various surfaces of medical devices, as so desired.

In accordance with the disclosed subject matter, a method of coating and folding an expandable member is provided. The method includes providing an expandable member with a plurality of folds defined therein, wherein the expandable member has a folded configuration and a fully expanded configuration at a rated nominal pressure. It is preferable that the select inflation pressure be sufficient to expose the surfaces of the expandable member desired to be coated. Particularly, it is beneficial to apply the coating to a fully inflated expandable member since a fully inflated expandable member provides a larger surface area to which a coating can be applied, thus allowing for a greater amount and efficacy of coating. Although various fluids are suitable for use in accordance with the disclosed subject matter, it is advantageous to employ a gaseous medium (e.g. air, oxygen, nitrogen, etc.) to ensure that there is no film or residue retained on the interior walls of the expandable member which can adversely affect the refolding process and final weight of the expandable member. Preferably, the expandable member is inflated at an initial pressure which is a percentage of a nominal inflation pressure, such as from about 20 to about 40% of nominal pressure, for a given balloon size/material. A coating is disposed on at least a portion of the expandable member.

In accordance with an aspect of the disclosed subject matter, and in order to realize the benefits of the expandable members described above, the initial inflation pressure is at least partially released or decreased to an intermediate pressure such that the expandable member is partially refolded after the desired coating is applied to the expandable member. The expandable member is partially deflated to an intermediate pressure by withdrawing an amount of inflation medium from the expandable member and applying an external force to the expandable member. For example, a select amount of inflation fluid or pressure, which is less than the initial inflation pressure contained within the expandable member during the coating process, is released or reduced to an intermediate pressure.

Figure 1:
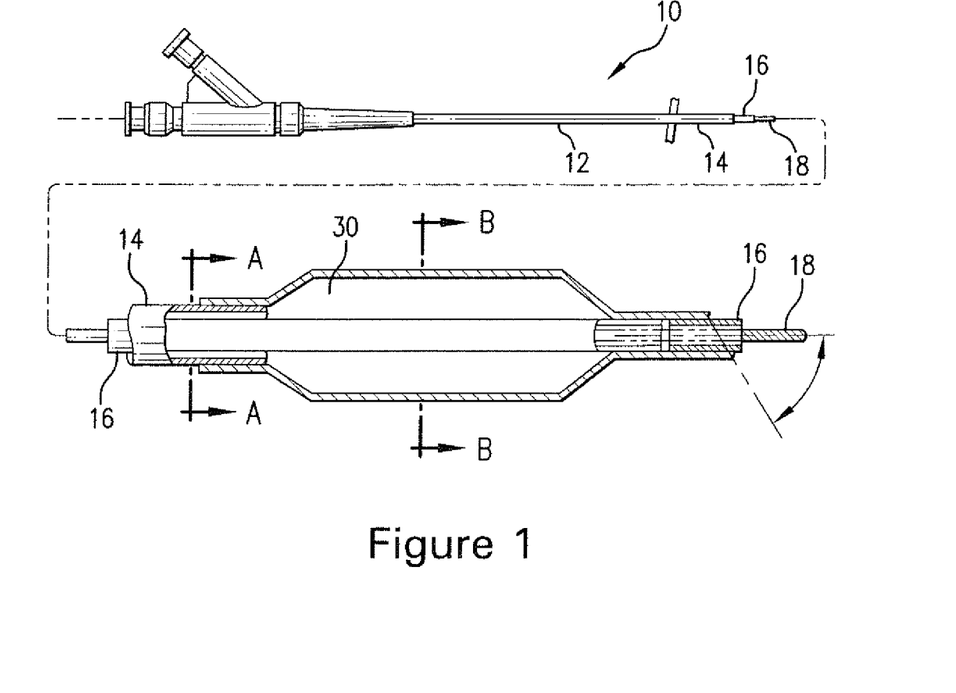
FIG. 1 is a schematic representation of an expandable member catheter in accordance with the disclosed subject matter.
Figure 1A:
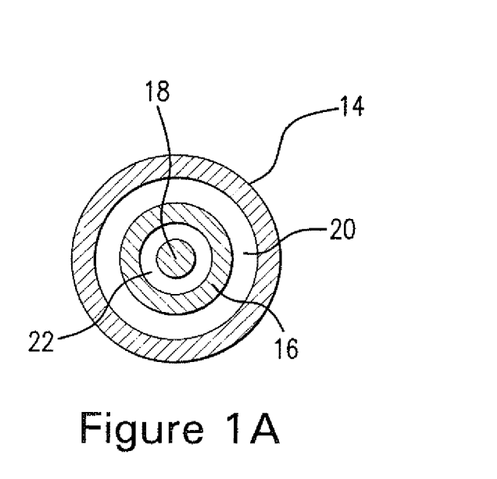
FIG. 1A is a schematic cross-sectional view taken along lines A-A in FIG. 1.
Figure 1B:
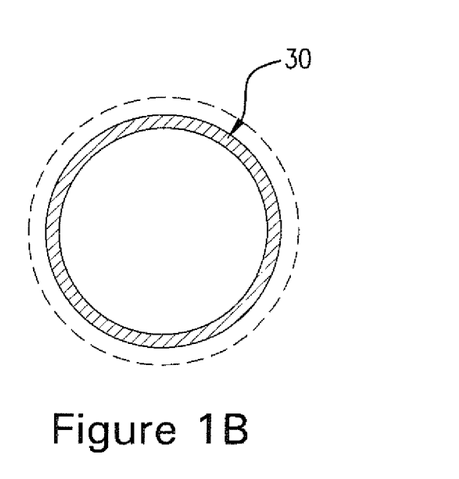
FIG. 1B is a schematic cross-sectional view taken along lines B-B in FIG. 1.
Figure 2:
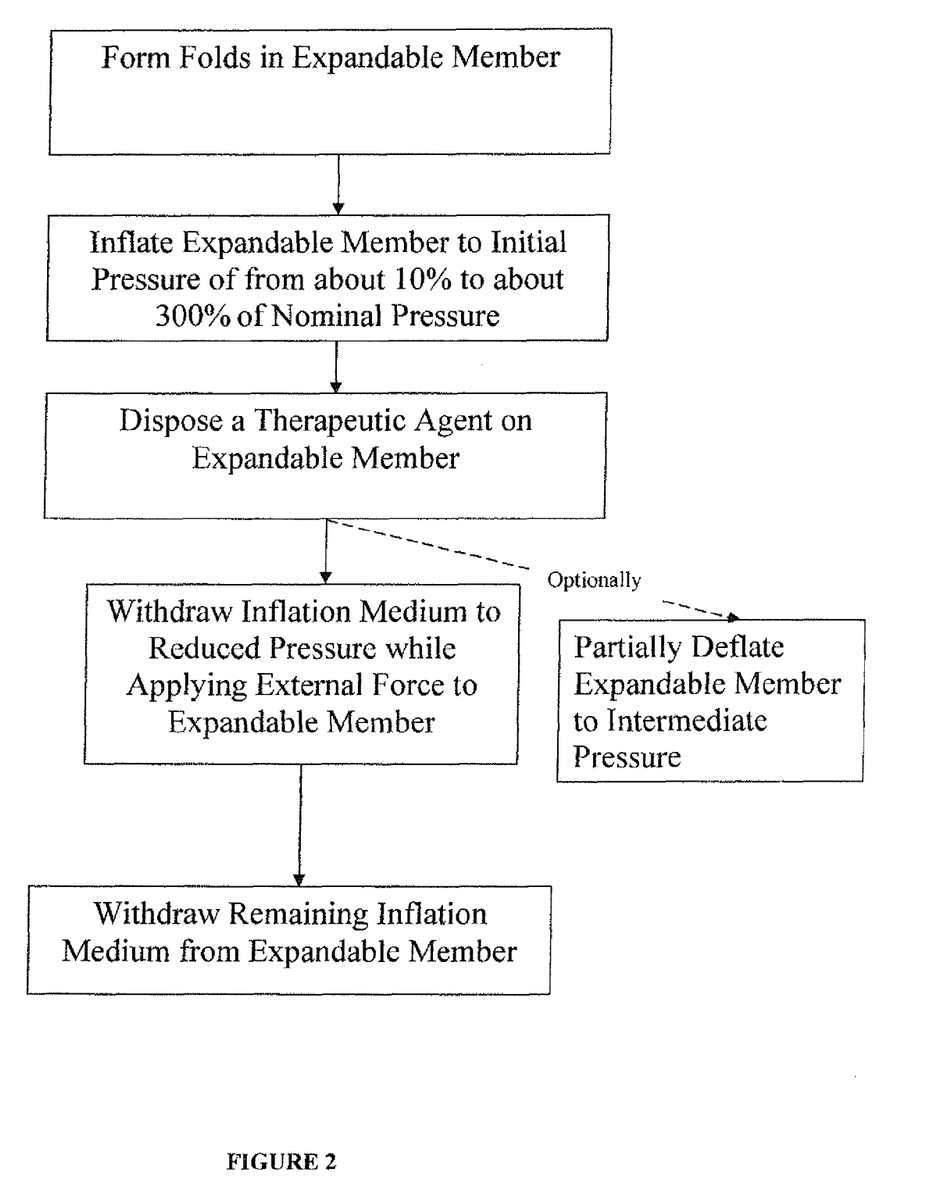
FIG. 2 is flow chart of the method in accordance with the disclosed subject matter.

For purpose of explanation and illustration, and not limitation an exemplary embodiment of a medical device having an expandable member is shown schematically in FIGS. 1A-B. Particularly, and as illustrated, the medical device embodied herein is a balloon catheter 10, which includes an elongated catheter shaft 12 having a proximal end and having a distal end and an expandable member 30 located proximate the distal end of the catheter shaft. The expandable member, or balloon as depicted herein, has an outer surface and an inner surface disposed at the distal end portion of the catheter shaft. In accordance with the disclosed subject matter, a coating is applied to at least a portion of the outer surface of the balloon.

The elongated catheter shaft 12 comprises an outer tubular member 14 and an inner tubular member 16. The outer tubular member 14 defines an inflation lumen 20 disposed between the proximal end portion and the distal end portion of the catheter shaft 12. Specifically, as illustrated in FIG. 1A, the coaxial relationship of this representative embodiment defines an annular inflation lumen 20 between the inner tubular member 16 and the outer tubular member 14. The expandable member 30 is in fluid communication with the inflation lumen 20. The inflation lumen can supply an inflation medium under positive pressure and can withdraw the inflation medium, i.e. provide negative pressure, from the expandable member. The expandable member 30 can thus be inflated and deflated. The elongated catheter is sized and configured for delivery through a tortuous anatomy, and can further include a guidewire lumen 22 that permits it to be delivered over a guidewire 18. As illustrated in FIG. 1A, the inner tubular member 16 defines the guidewire lumen 22 for the guidewire 18. Although FIGS. 1 and 1b illustrate the guidewire lumen as having a coaxial over-the-wire (OTW) construction, the guidewire lumen can be configured as dual lumen over-the-wire (OTW) or a rapid-exchange (RX) construction, as is well known in the art.

A wide variety of balloon catheters and balloon constructs are known and suitable for use in accordance with the disclosed subject matter. For example, the expandable member can be made from polymeric material such as compliant, non-compliant or semi-compliant polymeric material or polymeric blends. Examples of such suitable materials include, but are not limited to, nylon 12, nylon 11, nylon 9, nylon 6, nylon 6/12, nylon 6/11, nylon 6/9, and nylon 6/6, polyurethane, silicone-polyurethane. Examples of other balloon and catheter embodiments which can be employed in accordance with the disclosed subject matter include U.S. Pat. Nos. 4,748,982; 5,496,346; 5,626,600; 5,300,085, 6,406, 457 and application Ser. Nos. 12/371,426; 11/539,944; 12/371,422, each of which is hereby incorporated by reference in their entirety.

In accordance with the disclosed subject matter, any of a variety of fluid compositions can be applied to the expandable member. For example, the fluid can include a therapeutic agent for treatment of tissue. Examples of suitable therapeutic agents include anti-restenosis, pro- or anti-proliferative, anti-inflammatory, antineoplastic, antiplatelet, anti-mitotic, anti-coagulant, anti-fibrin, cytostatic, cytoprotective, ACE inhibiting, cardioprotective, antithrombotic, antimitotic, antibiotic, antiallergic and antioxidant compounds. Such therapeutic agents can be, again without limitation, a synthetic inorganic or organic compound, a protein, a peptide, a polysaccharides and other sugars, a lipid, DNA and RNA nucleic acid sequences, an antisense oligonucleotide, an antibodies, a receptor ligands, an enzyme, an adhesion peptide, a blood clot agent including streptokinase and tissue plasminogen activator, an antigen, a hormone, a growth factor, a ribozyme, and a retroviral vector. Preferably, however, the therapeutic agents include, cytostatic drug. The term "cytostatic" as used herein means a drug that mitigates cell proliferation but allows cell migration. These cytostatic drugs, include for the purpose of illustration and without limitation, macrolide antibiotics, rapamycin, everolimus, zotarolimus, biolimus A9, deforolimus, AP23572, tacrolimus, temsirolimus, pimecrolimus, structural derivatives and functional analogues of rapamycin, structural derivatives and functional analogues of everolimus, structural derivatives and functional analogues of zotarolimus and any marcrolide immunosuppressive drugs. The term "antiproliferative" as used herein means a drug used to inhibit cell growth, such as chemotherapeutic drugs. Some non-limiting examples of antiproliferative drugs include taxanes, paclitaxel, and protaxel.

Additionally or alternatively, the fluid can include other compounds or additives, such as binding agents, plasticizers, solvents, surfactants, additives, fillers, and the like. Examples of possible compounds include zotarolimus, polyvinylpyrrolidone and glycerol. In one embodiment the therapeutic agent can be provided in liquid form or dissolved in a suitable solvent. In another embodiment, therapeutic agent is provided as a particulate and mixed in a suitable carrier for application as a fluid.

In accordance with the disclosed subject matter, the expandable member of the medical device has a plurality of folds defined therein. For example, a number of conventional balloon catheters include such folds, so as to have a folded configuration and a fully expanded configuration. Generally, the formation of folds can be performed using heat and pressure to form or define creases in the material of the balloon. Examples of such folded balloons are disclosed, for purpose of illustration in U.S. Pat. Nos. 6,494,906; 6,478,807; and 5,911,452, each of which is hereby incorporated by reference in their entirety.

Particularly, a plurality of folds or pleats are initially imparted into a expandable member of a catheter by any means known in the art. This is accomplished by processing the expandable member in a pleat head that imparts a plurality of folds or pleats into the expandable member. After this, the pleated expandable member is processed in a fold head where the pleats are wrapped in on direction and compressed to reduce the overall profile. For example, the processing can be performed by an automated table top pleat and folder manufactured by Machine Solutions Inc. (MSI), MSI Balloon Form/Fold/Set Machine WS1275-101. In one embodiment, five folds of equivalent surface area are imparted into the expandable member which result in a symmetrical shape when in the folded, i.e. uninflated, configuration. Although the exemplary embodiment illustrated in the drawings depicts five folds, it is to be understood that the number and size of the folds can vary, as so desired, to expandable members of various dimensions and shapes. The folded configuration provides a reduced profile which facilitates assembly, storage and shipping of the catheter. Additionally, the reduced profile of the folded expandable member improves the deliverability and trackability of the catheter through the vascular anatomy.

The expandable member is inflated to an initial pressure of from about 10% to about 300% of nominal pressure. The initial pressure is preferably from about 20% to about 100% of nominal pressure. In one embodiment, during the inflation, initial pressure of the expandable member is less than nominal pressure. In one embodiment, the initial pressure is from about 20% to about 40% of nominal pressure. In one embodiment, the nominal pressure is about 6 atmospheres to about 8 atmospheres.

With the desired number of folds imparted in the expandable member, the expandable member is inflated to an initial pressure of from about 20% to about 40% of nominal pressure, and fluid such as a therapeutic agent is disposed thereon. To assist with the application of the therapeutic agent on the surface of the expandable member, a mandrel can be inserted within the guidewire lumen 22. The mandrel can be constructed from a variety of materials, e.g. metal, metal alloys, and polymeric materials having sufficient rigidity to maintain the catheter in a linear alignment. In this regard, the mandrel serves to inhibit or prevent bowing or warping of the catheter and expandable member. Accordingly, the expandable member is maintained in a consistent and linear alignment about the longitudinal axis of the catheter, which in turn can allow for a uniform coating of therapeutic agent along the desired length of the expandable member. Furthermore, maintaining the expandable member in a fixed profile and linear alignment can assist in minimizing waste of therapeutic agent during the coating process, e.g., spraying, dipping, direct fluid coating, etc. If coating is to be performed on an assembled catheter, the mandrel can have a length to extend the entire length of the catheter and an outer diameter sized to be positioned within the guidewire lumen 22.

One or more coatings can be applied to the select portions of the medical device by processes such as spraying, dipping, syringe coating, electrospinning, electrostatic coating, direct coating, direct fluid application as disclosed in Application Ser. No. 61/345,575, combinations thereof, or other means as known to those skilled in the art. The coating can be applied over at least a portion or the entirety of the expandable member or medical device in non-uniform, or uniform concentrations and/or patterns. The coating characteristics can be affected by process variables. For example, for dip-coating process, coating quality and thickness can vary as an effect of variables such as number, rate, and depth of dips along with drying time and temperature. Accordingly, the variables of the particular coating process employed can be controlled to achieve the desired coating characteristics. By way of example, and not limitation, certain coating processes that can be used with the instant invention are described in U.S. Pat. No. 6,669,980 to Hansen; U.S. Pat. No. 7,241,344 to Worsham; and U.S. Publication No. 20040234748 to Stenzel, the disclosures of which are hereby incorporated by reference in their entirety.

In accordance with the disclosed subject matter, the expandable member is partially or fully inflated to an initial pressure of from about 20% to about 40% of nominal pressure when the fluid is disposed thereon. The extent in which the expandable member is inflated will depend at least in part on the amount of inflation medium selected for initial inflation. It therefore is preferable that the select amount of inflation medium be sufficient to expose the surfaces of the expandable member desired to be coated. Particularly, it is beneficial to apply the coating to a fully inflated expandable member since a fully inflated expandable member provides a larger surface area to which a coating can be applied, thus allowing for a greater amount and efficacy of coating. Although various fluids are suitable for use in accordance with the disclosed subject matter, it is advantageous to employ a gaseous medium, e.g. air, to ensure that there is no film or residue retained on the interior walls of the expandable member which can adversely affect the refolding process and final weight of the expandable member.

In accordance with an aspect of the disclosed subject matter, and in order to realize the benefits of the reduced profile expandable members described above, the expandable member is refolded after the desired coating is applied to the expandable member. To avoid detrimental impact to the applied coating during the refolding process, the expandable member is first partially deflated to an intermediate pressure by withdrawing an initial amount of inflation medium and applying an external force to the expandable member. Particularly, an amount of fluid, which is less than the select amount of fluid contained within the expandable member during the coating process, is withdrawn from the expandable member to partially deflate the expandable member. The external force is applied to the outer surface of the expandable member, preferably simultaneously while withdrawing the initial amount of inflation medium, to facilitate the deflation and provide a circumferential constraint on the expandable member. The interaction of the initial, intermediate, or deflation and the application of the external force effect the reformation of the previously defined folds and ensure a symmetrical expandable member profile when in the deflated configuration. Further, and as discussed above, a mandrel can be inserted into the guidewire lumen 22 of the catheter. The mandrel serves to inhibit or prevent bowing or warping of the catheter and expandable member, and maintains the diameter and shape of the expandable member is maintained during exposure to the external force. Accordingly, the expandable member is maintained in a consistent and linear alignment about the longitudinal axis of the catheter, which in turn allows the therapeutic agent to dry in a consistent and uniform fashion on the surface of the expandable member, thus maximizing the efficacy of the therapeutic agent. The mandrel can be configured to extend at least the length of the expandable member, and an outer diameter for positioning within the guidewire lumen 22.

The release of the amount of fluid, or inflation pressure, can be performed by exposing the expandable member to ambient conditions. That is, the expandable member in its partially expanded configuration and initial inflation pressure will have an elevated pressure as compared to the ambient conditions. Accordingly, upon release of the initial amount of fluid, or initial inflation pressure, by exposure to the ambient conditions, the pressure differential will cause at least some of the amount of fluid contained within the expandable member to exit and reduce the pressure within the expandable member to an intermediate pressure.

The intermediate pressure is from about 10% to 50% of nominal pressure, and preferable, the intermediate pressure is from about 10% to about 20% of nominal pressure. Thus, the expandable member will partially deflate and partially refold with minimal surface tension exhibited on the coating disposed on the surface of the expandable member. The operator can perform an analysis to determine if drug retained on expandable member meets minimum criteria, for example, visual inspection for checking bare spots on the expandable member.

Additionally, or alternatively, a negative pressure, for example, between about 0.1 atmosphere (atm) to about 0.25 atm, can be drawn on the expandable member to reduce the pressure to an intermediate pressure and thus partially deflate the expandable member. In embodiments in which a negative pressure is applied to release the initial amount of fluid, or reduce the initial inflation pressure to the intermediate pressure, the negative pressure is less than the vacuum pressure required to withdraw the entire amount of fluid, or initial inflation pressure, in the expandable member and thus return the expandable member to the completely folded or collapsed condition. The pressure of the expandable member can be controlled to be independently optimized such that the rate of inflation and/or depressurization can be adjusted either continuously or via a step-wise function.

For purpose of withdrawing an amount of inflation medium, a number of known techniques can be used. For example, and as embodied herein, a deflation device such as a syringe pump, having a gas-tight syringe can be attached to the inflation lumen of the expandable member. The deflation device allows for automated, repeatable, and controlled amount of fluid withdrawn by volume from the expandable member. This is advantageous since it reduces or eliminates the variability inherent in a human operator controlled method or apparatus. Alternative devices and techniques can be used for withdrawing desired amounts of inflation medium. Withdrawing inflation medium can occur at a rate of approximately 2 ml/min or less.

With regard to the application of external force on the expandable member, a variety of known techniques can be used. Particularly, the external force can be applied mechanically, hydraulically or pneumatically. For example, pneumatic force can be applied using a pressure chamber of suitable construct to induce a positive pressure on the external surface of the expandable member. Similarly, hydraulic pressure can be applied using suitable liquid that will not interact with the applied coating, or by providing a sheath to protect the applied coating. In this manner, the external force can be applied as substantially uniform pressure across the surface of the expandable member.

Figure 8:
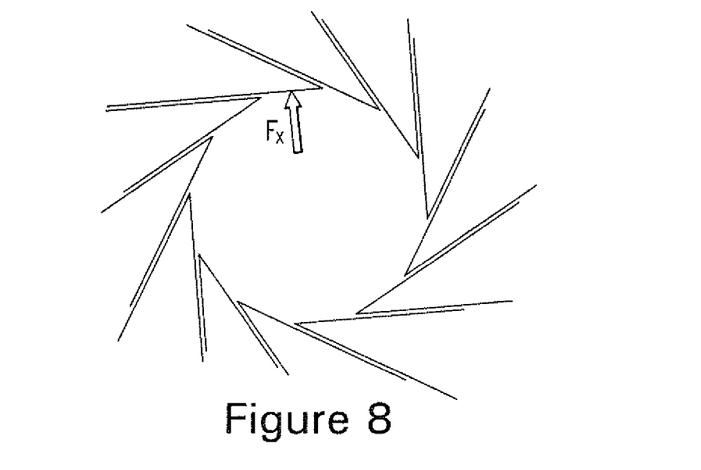
FIG. 8 is a schematic representation of a iris for imparting an external force in accordance with the disclosed subject matter.

As embodied herein, for purpose of illustration and not limitation, the external force is applied mechanically. In this manner the external force can include a torsional component to assist with the wrapping and folding of the folds. Furthermore, if desired, the mechanical force can be applied at select locations to minimize any risk of damage to the coating while obtaining the advantage of the external force. For example, a stent crimper or similar apparatus can be used for applying an external force. The stent crimper includes a plurality of jaws which allow for circumferential constraint of the expandable member. The jaws of the stent crimper can be configured to circumscribe the entire outer surface of the expandable member, or alternatively, have discrete points of contact with the expandable member. For example, a stent crimper can apply an external force to an expandable member with a rate of from about 0.2 to about 0.25 psi per mm of the expandable member. Alternatively, the external force can be applied using a plurality of blades and configured with a cam or actuator to contract the blades in unison, i.e. simultaneously, such as an iris as illustrated in FIG. 8. The blades can be arranged to contact the expandable member over the entire working length of the expandable member, or alternatively, at discrete locations.

Accordingly, the jaws or blades can exert a substantially uniform or non-uniform force along the expandable member, as so desired. In this manner, the stent crimper, or other suitable device, represents the sole piece of equipment which contacts the coating disposed on the expandable member. As compared to prior art techniques, this discrete point of contact is advantageous as it minimizes the risk of damage or degradation to the coating surface. As previously noted, it is preferable for the external force to be applied simultaneously while withdrawing the initial amount of inflation medium. Similarly, it is preferred that such application of external force be performed uniformly throughout the withdrawing process, but with only sufficient force to refold the folds of the expandable member. The external force preferably should not overcome the withdrawing process, i.e., the external force should not force inflation medium from the expandable member or otherwise crush the expandable member.

For purpose of example, and again with reference to the stent crimper, it is suitable to use a lever arm to actuate the jaws to close via gravitational forces. This is advantageous in that it results in minimal force on the expandable member, and relatively low pressure and temperature acting on the coating to thereby minimize the risk of damage or degradation of the coating. Alternatively, the jaws can be actuated hydraulically or pneumatically to induce a greater force on the expandable member, if so desired.

Further in accordance with the disclosed subject matter, a remaining amount of inflation medium is withdrawn after partially deflating the expandable member. For example, and as embodied herein, an indeflator or vacuum box is provided to draw a vacuum on the expandable member. The indeflator or vacuum box is placed in fluid communication with the inflation lumen of the expandable member, after partial deflation of the expandable member by withdrawing an initial amount of fluid medium and application of an external force as described above, a remaining or residual fluid is withdrawn to return the expandable member to the folded configuration.

Reference will now be made to the system of the disclosed subject matter, and the operation of the system. Particularly, and for purpose of illustration and not limitation, a suitable system for performing the method previously described includes the following.

In operation, a 5 cc glass tight syringe pump of the deflation device is attached to a 3-way stopcock, with the two remaining ports being attached to the vacuum source and catheter, respectively. The stopcock is open to the syringe and the proximal inflation luer of the catheter to establish a closed system. The jaws of the closure device, e.g. stent crimper, are opened to receive the inflated expandable member therein. The jaws can be configured to receive a variety of expandable member diameters, and extend a length equal to or greater than the length of the expandable member.

Figure 3:
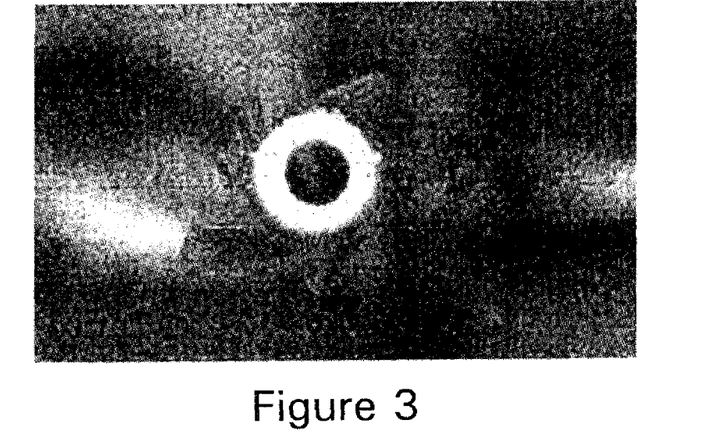
FIG. 3 is a schematic axial view of an expandable member folded with uneven folds referred to as "pancaking".

As disclosed above, the jaws serve to circumferentially constrain the expandable member. This constraint prevents any portions of the expandable member from collapsing or refolding unevenly or "pancaking" which results in an asymmetrical profile, and uneven expansion rate of the folds upon expandable member inflation within the lumen. Additionally, the circumferential constraint prevents undesired bowing or sagging of the expandable member along its longitudinal axis. An example of this uneven refolding or "pancaking" is illustrated in FIG. 3. To further minimize or prevent "pancaking" and assist in returning the initial folds to their original direction, the external force applied by the jaws can include a torsional component which wraps or rolls the folds in an overlapping manner to minimize the profile of the expandable member.

Upon closure of the jaws around the inflated expandable member and application of the constraining force on the outer surface of the expandable member, the deflation device gradually withdraws a predetermined amount of fluid from the expandable member at a predetermined rate to partially deflate the expandable member. In other words, the withdrawal of the amount of fluid and the application of the external force occurs simultaneously. The particular amount and rate of withdrawal can vary depending on the coating properties. For example, a volume of about 0.75 ml of fluid can be withdrawn at a rate of about 2 ml/min or less for a 6×40 mm balloon. In accordance with the disclosed subject matter, the initial amount of fluid withdrawn is about 60-80% of the fluid required to inflate the expandable member to the fully expanded configuration at a rated nominal pressure.

As the deflation device is arranged to only partially deflate the expandable member, the amount of fluid withdrawn from the expandable member is less than the total amount of fluid contained within the expandable member when in the inflated configuration.

Figure 4A:
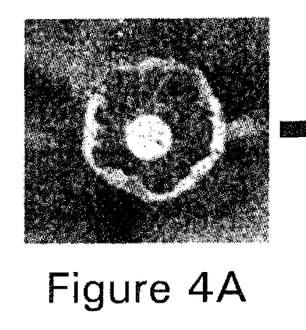
FIGS. 4A-B are schematic axial views of an expandable member which is refolded without application of an external force of the disclosed subject matter.
Figure 4B:
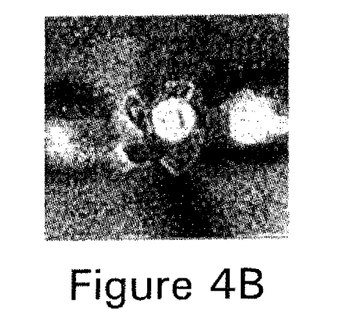
Figure 5A:
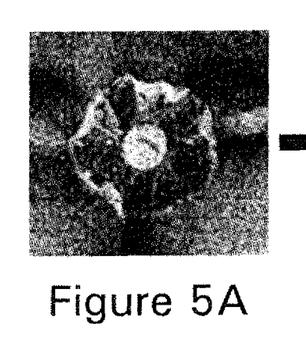
FIGS. 5A-B are schematic axial views of an expandable member which is refolded with application of an external force of the disclosed subject matter.
Figure 5B:
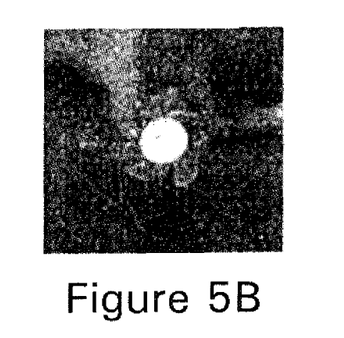

After partially deflating the expandable member by withdrawing the initial amount of fluid and closure of the jaws, the expandable member can be inspected to ensure proper refolding has occurred and no "pancaking" effects are present, FIGS. 4A-B provide an illustrative example of a expandable member which is refolded without the closure device, e.g. stent crimper. By comparison, FIGS. 5A-B provide an illustrative example of a expandable member which is refolded with the closure device, e.g. stent crimper in accordance with the disclosed subject matter. As is evident, the expandable member of FIGS. 5A-B which is refolded in accordance with the disclosed subject matter achieves an even and symmetrical, i.e. cylindrical, shape. In the event that pancaking effects are detected during the inspection, the expandable member can be inflated again and the above-described process can be repeated to achieve an even, symmetrical refolded expandable member. In this regard, the disclosed subject matter is advantageous in that it allows for "pancaked" expandable members to be "re-worked" or reprocessed to achieve the proper symmetrical shape rather than discarded.

If no "pancaking" is detected, the vacuum source can be activated to withdraw the remaining amount of fluid within the expandable member to fully collapse the expandable member. In some embodiments a sheath can be placed over the expandable member. In such embodiments, one end of the sheath can be flared, in order to facilitate insertion of the expandable member therein and avoid any undesired snagging, and placed over the distal end of the expandable member. Additionally, a lubricious coating can be applied to reduce the frictional forces, provided the lubrication employed does not interfere or compromise the efficacy of the therapeutic agent. The sheath is slid over the expandable member a desired distance, until significant resistance is felt. Once the sheath is in the desired position, the stopcock is opened to the vacuum source, e.g. indeflator and a full vacuum is pulled to remove all residual fluid in the expandable member. The remainder of the sheath can then be advanced over the expandable member to ensure that no wrinkles or unwanted folds are present and that the drug coating is protected.

Figure 6:
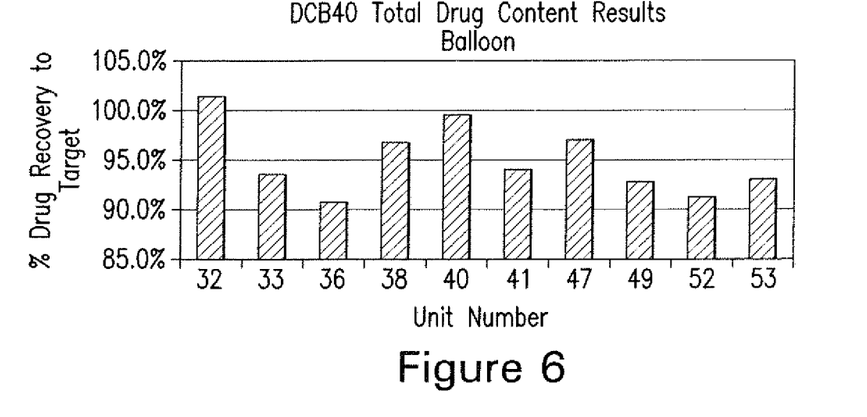
FIG. 6 is a graphical representation of the coating content of the expandable member after a sterilization process.

The methods and apparatus of the disclosed subject matter provide an additional benefit in terms of drug recovery from the folded expandable members. FIG. 6 shows data from devices that were processed using the methods disclosed. The graph depicts total drug content on the balloon after the sheath is removed and demonstrates that minimal drug is lost from the method disclosed herein. Current specifications for drug content are +/−20% from a 100% target. It is possible that particular samples have more than 100% drug as there is acceptable variability on the method for which the coating is deposited as well as acceptable variability on the analytical method used to determine drug content.

Figure 7:
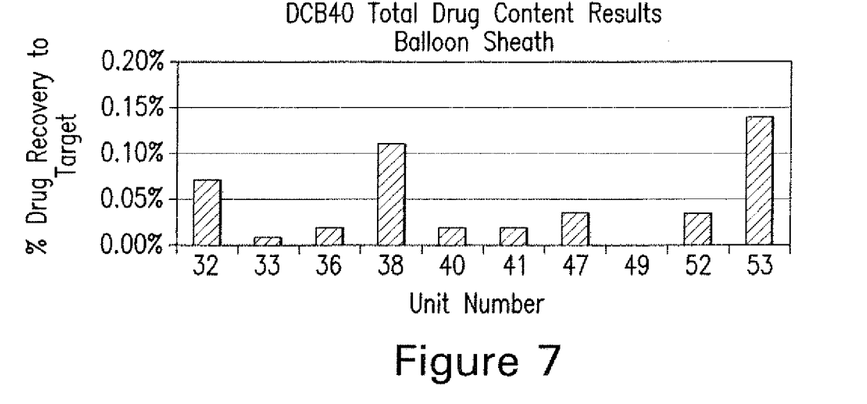
FIG. 7 is a graphical representation of the coating content of the sheath after a sterilization process.

In accordance with another aspect of the disclosed subject matter, the fully assembled catheter can undergo a sterilization process. For purpose of evaluation, a study was performed to determine the effectiveness of the presently disclosed method and system. A group of Nylon/Pebax 72D blend balloons (size 6×40 mm) were tested in this study. A 600 μg/cm$^2$ dose of zotarolimus/poly(N-vinyl pyrrolidone) (PVP)/glycerol (ZPG) formulation was applied to the balloons. After sterilization, the expandable member and sheath were removed from the catheter and are independently analyzed to determine the coating content, i.e., the amount of coating retained on the surface as a percentage of the total amount of coating dispensed during application of the coating to the expandable member. FIGS. 6-7 graphically depict the coating content of the expandable member and sheath, respectively, for a representative example performed using the method and system previously described. As illustrated, the method and apparatus of the disclosed subject matter provide about 90-100% drug recovery on the expandable member itself, while less than about 2% of the drug is retained on the sheath.

In accordance with in the disclosed subject matter, an endoprosthesis, e.g. stent, can be mounted on the expandable member. The type of stent that can be used includes, but is not limited to, bare metal stent, drug eluting stent, prohealing stent, and self-expanding vulnerable plaque implant. The stent coating can contain the same or different therapeutic agents from the catheter or expandable member. Similarly, the coating on the catheter or expandable member can have the same or distinct release kinetics from the therapeutic coating on the stent. The coating applied to the expandable member can be allowed to dry prior to placement of the stent thereon.

Alternatively, the coating could not be allowed to dry or cure past a "tacky" state before the stent is positioned and/or crimped onto it. This would enable the adhesion of the coating on the expandable member to the inside of the prosthesis. This process increases the retention of the prosthesis onto the expandable member (acting as a prosthesis retention enhancer) thus reducing the chance that the stent will move on the expandable member during the torturous delivery through the vascular lumen.

If desired, and as previously discussed, a protective sheath can be provided to protect the coating during shipping and storage and/or during delivery of the coated expandable member through the body lumen. A variety of sheaths are known, including removable sheaths or balloon covers, retractable sheaths to be withdrawn prior to deployment of the balloon, and elastic sheaths that conform to the balloon upon expansion. Such elastic sheaths are porous or include apertures along a portion thereof. In operation, the inflation of the expandable member causes the sheath to expand for release of the coating and/or therapeutic agent through the porous wall or apertures to the tissue of the arterial wall. For example, see U.S. Pat. No. 5,370,614 to Amundson, the disclosure of which is incorporated by reference in its entirety While the disclosed subject matter is described herein in terms of certain preferred or exemplary embodiments, those skilled in the art will recognize that various modifications and improvements can be made to the disclosed subject matter without departing from the scope thereof. Moreover, although individual features of one embodiment of the disclosed subject matter can be discussed herein or shown in the drawings of the one embodiment and not in other embodiments, it should be apparent that individual features of one embodiment can be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

The invention claimed is:

1. A system for coating an expandable member having a plurality of folds defined therein, the expandable member having a folded configuration and a fully expanded configuration at a rated nominal pressure, the system comprising:
   an inflator adapted to inflate an expandable member to an initial pressure between about 10% to about 300% of the rated nominal pressure;
   a dispenser to dispose a therapeutic agent on at least a portion of the expandable member inflated to the initial pressure; and
   a deflation assembly at least to partially deflate the inflated expandable member with the therapeutic agent disposed thereon to an intermediate pressure, the deflation assembly configured to withdraw an amount of inflation medium from the inflated expandable member and to apply an external force having a torsional component to the expandable member simultaneous with or subsequent to partially deflating the expandable member to refold the plurality of folds of the expandable member toward the folded configuration.

2. The system of claim 1, wherein the normal pressure is from about 6 to about 8 atmospheres.

3. The system of claim 1, wherein the initial pressure of the expandable member is from about 20% to about 100% of nominal pressure.

4. The system of claim 1, wherein the initial pressure of the expandable member is from about 20% to about 40% of nominal pressure.

5. The system of claim 1, wherein the dispenser is a sprayer, dipper, syringe, electrostatic coating assembly, electrospinning assembly or direct coating assembly.

6. The system of claim 1, wherein the therapeutic agent is selected from the group consisting of everolimus, zotarolimus, rapamycin, biolimus, myolimus, novolimus, deforolimus, tacrolimus, temsirolimus, pimecrolimus, paclitaxel, protaxel, taxanes, or a combination thereof.

7. The system of claim 1, wherein the deflation assembly includes a syringe pump.

8. The system of claim 1, wherein the deflation assembly withdraws the initial amount of inflation medium at a rate of approximately 2 ml/min or less.

9. The system of claim 1, wherein the intermediate pressure is from about 10% to about 50% of nominal pressure.

10. The system of claim 1, wherein the intermediate pressure is from about 10% to about 20% of nominal pressure.

11. The system of claim 1, wherein the external force is applied to the expandable member mechanically, hydraulically or pneumatically.

12. The system of claim 1, wherein the external force is applied as a substantially uniform force.

13. The system of claim 1, wherein the external force is applied at select locations to the expandable member.

14. The system of claim 1, wherein the deflation assembly includes a stent crimper with a rate of from about 0.2 to about 0.25 psi per mm to apply the external force.

15. The system of claim 1, wherein the deflation assembly withdraws the inflation medium and applies the external force simultaneously.

16. The system of claim 1, further comprising a vacuum source to withdraw a remaining amount of inflation medium from an expandable member.

17. The system of claim 16, wherein the vacuum source is a vacuum box or indeflator.

18. The system of claim 1, wherein the inflation medium is a gas.

19. The system of claim 1, further comprising a mandrel disposed within a lumen of the expandable member.

20. A medical device comprising:
   an expandable member with a plurality of folds defined therein, the expandable member having a folded configuration and an expanded configuration at a rated nominal pressure, the expandable member having a surface with a coating of therapeutic agent on at least a portion thereof, the coating being applied on the surface by:
   inflating the expandable member to an initial pressure of from about 10% to about 300% of nominal pressure,
   disposing a therapeutic agent on at least a portion of the expandable member,
   partially deflating the expandable member with the therapeutic agent disposed thereon to an intermediate pressure, wherein partially deflating the expandable member includes withdrawing an amount of inflation medium from the expandable member, and
   applying an external force having a torsional component to the expandable member simultaneous with or subsequent to partially deflating the expandable member to refold the plurality of folds of the expandable member toward the folded configuration.

21. The medical device of claim 20, wherein applying the external force further includes applying the external force with a stent crimper with a rate of from about 0.2 to about 0.25 psi per mm.

22. A system for coating an expandable member having a plurality of folds defined therein, the system comprising:
   an inflator to inflate an expandable member to an initial pressure, the initial pressure being from about 10% to about 300% of a rated nominal pressure;
   a dispenser to dispose a therapeutic agent on at least a portion of an expandable member inflated to the initial pressure; and
   a deflation assembly at least to partially deflate the inflated expandable member to an intermediate pressure, the deflation assembly configured to withdraw an amount of inflation medium from the inflated expandable member and to apply an external force to an expandable member, wherein the deflation assembly includes a stent crimper with a rate of from about 0.2 to about 0.25 psi per mm to apply the external force.

* * * * *